(12) United States Patent  (10) Patent No.: US 8,963,105 B2
Kishima  (45) Date of Patent: Feb. 24, 2015

(54) IMAGE OBTAINING APPARATUS, IMAGE OBTAINING METHOD, AND IMAGE OBTAINING PROGRAM

(71) Applicant: Sony Corporation, Tokyo (JP)

(72) Inventor: Koichiro Kishima, Kanagawa (JP)

(73) Assignee: Sony Corporation, Tokyo (JP)

( * ) Notice: Subject to any disclaimer, the term of this patent is extended or adjusted under 35 U.S.C. 154(b) by 98 days.

(21) Appl. No.: 13/667,730

(22) Filed: Nov. 2, 2012

(65) Prior Publication Data

US 2013/0119272 A1  May 16, 2013

(30) Foreign Application Priority Data

Nov. 15, 2011  (JP) .................................. 2011-249866

(51) Int. Cl.
*G02B 21/16* (2006.01)
*G01N 21/64* (2006.01)
*G02B 21/24* (2006.01)
*G02B 21/36* (2006.01)

(52) U.S. Cl.
CPC ............ *G01N 21/6428* (2013.01); *G02B 21/16* (2013.01); *G02B 21/241* (2013.01); *G02B 21/367* (2013.01)
USPC ...................................... 250/458.1

(58) Field of Classification Search
USPC ........................................... 250/458.1
See application file for complete search history.

(56) References Cited

U.S. PATENT DOCUMENTS 6,388,809 B1 *  5/2002  MacAulay ..................... 359/383

FOREIGN PATENT DOCUMENTS

JP  2011-017982  1/2011

\* cited by examiner

*Primary Examiner* — David Porta
*Assistant Examiner* — Edwin Gunberg
(74) *Attorney, Agent, or Firm* — K&L Gates LLP

(57) ABSTRACT

An image obtaining apparatus includes: a light source configured to irradiate a biological sample having a fluorescent label with an excitation light, the excitation light exciting the fluorescent label; an optical system including an objective lens, the objective lens being configured to magnify an imaging target of the biological sample; an image sensor configured to form an image of the imaging target magnified by the objective lens; a movement controller configured to move a focus position of the optical system in an extended range, the extended range being obtained by adding predetermined margins to both ends of the imaging target in a thickness range; and a light-exposure controller configured to expose the image sensor to light while moving the focus position of the optical system in the extended range.

6 Claims, 9 Drawing Sheets

FIG.10

| Cell nucleus No. | Color | Bright point No. | Brightness average | Area |
|---|---|---|---|---|
| 1 | Green | 1 | 100 | 105 |
| | | 2 | 120 | 100 |
| | Red | 1 | 110 | 120 |
| | | 2 | 105 | 115 |
| 2 | Green | 1 | 200 | 200 |
| | | 2 | 260 | 210 |
| | Red | 1 | 220 | 220 |
| | | 2 | 215 | 200 |

IMAGE OBTAINING APPARATUS, IMAGE OBTAINING METHOD, AND IMAGE OBTAINING PROGRAM

CROSS REFERENCES TO RELATED APPLICATIONS

The present application claims priority to Japanese Priority Patent Application JP 2011-249866 filed in the Japan Patent Office on Nov. 15, 2011, the entire content of which is hereby incorporated by reference.

BACKGROUND

The present disclosure relates to an image obtaining apparatus, an image obtaining method, and an image obtaining program obtaining an image by using a microscope.

Flow cytometry is known as a method of analyzing and sorting minute particles such as biological tissues. A flow cytometry apparatus (flow cytometer) is capable of obtaining, at high speed, shape information and fluorescence information from each particle such as a cell. The shape information includes size and the like. The fluorescence information is information on DNA/RNA fluorescence stain, and on protein and the like dyed with fluorescence antibody. The flow cytometry apparatus (flow cytometer) is capable of analyzing correlations thereof, and of sorting a target cell group from the particles. Further, imaging cytometry is known as a method of performing cytometry based on a fluorescent image of a cell. In the imaging cytometry, a fluorescent image of a biological sample on a glass slide or a dish is magnified and photographed. Information on each cell in the fluorescent image is digitalized and quantified. The information includes, for example, an intensity (brightness), size, and the like of bright points, which mark a cell. Further, the cell cycle is analyzed, and other processing is performed.

In a case of obtaining a fluorescent image of a biological sample, which is fluorescence-stained, the focus is moved at predetermined distances in the thickness direction of the biological sample. Each of fluorescent images at the plurality of focuses is generated as image data. As a result, all the bright points, which mark a target cell, may be reliably obtained. However, in this case, the number of fluorescent images for one biological sample is extremely large. Further, there is a tendency that processing load and data volume for one biological sample are increased.

If a distance between focus positions is made larger, the number of fluorescent images for one biological sample is decreased. However, in this case, some bright points, which mark target cells, may not be obtained. As a result, analysis accuracy is lowered. Further, the following case is discussed. That is, the focus depth of the objective lens is increased by lowering the NA of an objective lens or by another method. However, in this case, the resolutions of all the fluorescent images are decreased uniformly. As a result, analysis accuracy is lowered after all.

In relation to the above-mentioned circumstances, for example, Japanese Patent Application Laid-open No. 2011-017982 discloses a method of obtaining a fluorescent image as follows. According to this method, a fluorescent-image obtaining unit moves a movable stage in a Z-axis direction (optical-axis direction), and moves the focus of an optical system on a sample site in the thickness direction. The fluorescent-image obtaining unit exposes an image sensor to light from the time point when the movement of the movable stage in the Z-axis direction is started to the time point when the movement of the movable stage is finished. The fluorescent-image obtaining unit obtains a fluorescent image of a sample site from the image sensor. The fluorescent image is an image obtained as the result of the light-exposure and obtained at the final time point.

SUMMARY

According to the technology of Japanese Patent Application Laid-open No. 2011-017982, it is possible to take one image, which is obtained by merging images of the entire biological sample as an imaging target at a plurality of focus positions in the thickness direction of the biological sample. As a result, images of all the bright points are obtained. The bright points exist in the entire biological sample in the thickness direction. However, the images of the bright points are blurred.

As described above, an image is obtained by continuously exposing the image sensor to light while moving the focus position over the entire biological sample in the thickness direction. In fact however, in the image, the bright points, which exist in the both ends of the biological sample in the thickness direction, are larger in size and lower in brightness than the bright points, which exist in the center portion. As a result, accuracy of measuring brightness, size, and the like of bright points may be lowered.

In view of the above-mentioned circumstances, it is desired to provide an image obtaining apparatus, an image obtaining method, and an image obtaining program, which may improve accuracy of detecting fluorescent labels.

According to an embodiment of the present technology, there is provided an image obtaining apparatus, including: a light source configured to irradiate a biological sample having a fluorescent label with an excitation light, the excitation light exciting the fluorescent label; an optical system including an objective lens, the objective lens being configured to magnify an imaging target of the biological sample; an image sensor configured to form an image of the imaging target magnified by the objective lens; a movement controller configured to move a focus position of the optical system in an extended range, the extended range being obtained by adding predetermined margins to both ends of the imaging target in a thickness range; and a light-exposure controller configured to expose the image sensor to light while moving the focus position of the optical system in the extended range.

In the image obtaining apparatus, it is preferable that the predetermined margins at the both sides of the imaging target in the thickness range be the same.

The image obtaining apparatus may further include a light source configured to irradiate a fluorescent label with an excitation light.

The light-exposure controller may be configured to expose the image sensor to light while moving the focus position of the optical system in the extended range, to thereby obtain a fluorescent image of the imaging target.

The image obtaining apparatus may further include an analyzer configured to detect the fluorescent label from the obtained fluorescent image, and to obtain the brightness and size of the fluorescent label.

According to another embodiment of the present technology, there is provided an image obtaining method, including: irradiating a biological sample having a fluorescent label with an excitation light, the excitation light exciting the fluorescent label; moving a focus position of an optical system in an extended range, the extended range being obtained by adding predetermined margins to both ends of an imaging target of the biological sample in a thickness range, the optical system including an objective lens, the objective lens being configured to magnify the imaging target; and exposing the image sensor to light while moving the focus position of the optical system in the extended range.

According to another embodiment of the present technology, there is provided an image obtaining program, configured to cause a computer to execute the steps of:

irradiating a biological sample having a fluorescent label with an excitation light from a light source, the excitation light exciting the fluorescent label;

moving a focus position of an optical system in an extended range, the extended range being obtained by adding predetermined margins to both ends of an imaging target of the biological sample in a thickness range, the optical system including an objective lens, the objective lens being configured to magnify the imaging target; and exposing the image sensor to light while moving the focus position of the optical system in the extended range.

As described above, according to the present technology, accuracy of detecting fluorescent labels may be improved.

Additional features and advantages are described herein, and will be apparent from the following Detailed Description and the figures.

BRIEF DESCRIPTION OF THE FIGURES

FIG. 10 is a recording example of results of detecting fluorescent markers by the image obtaining apparatus of FIG. 1;

DETAILED DESCRIPTION

Hereinafter, an embodiment of the present disclosure will be described with reference to the drawings.

First Embodiment

Structure of Image Obtaining Apparatus

Figure 1:
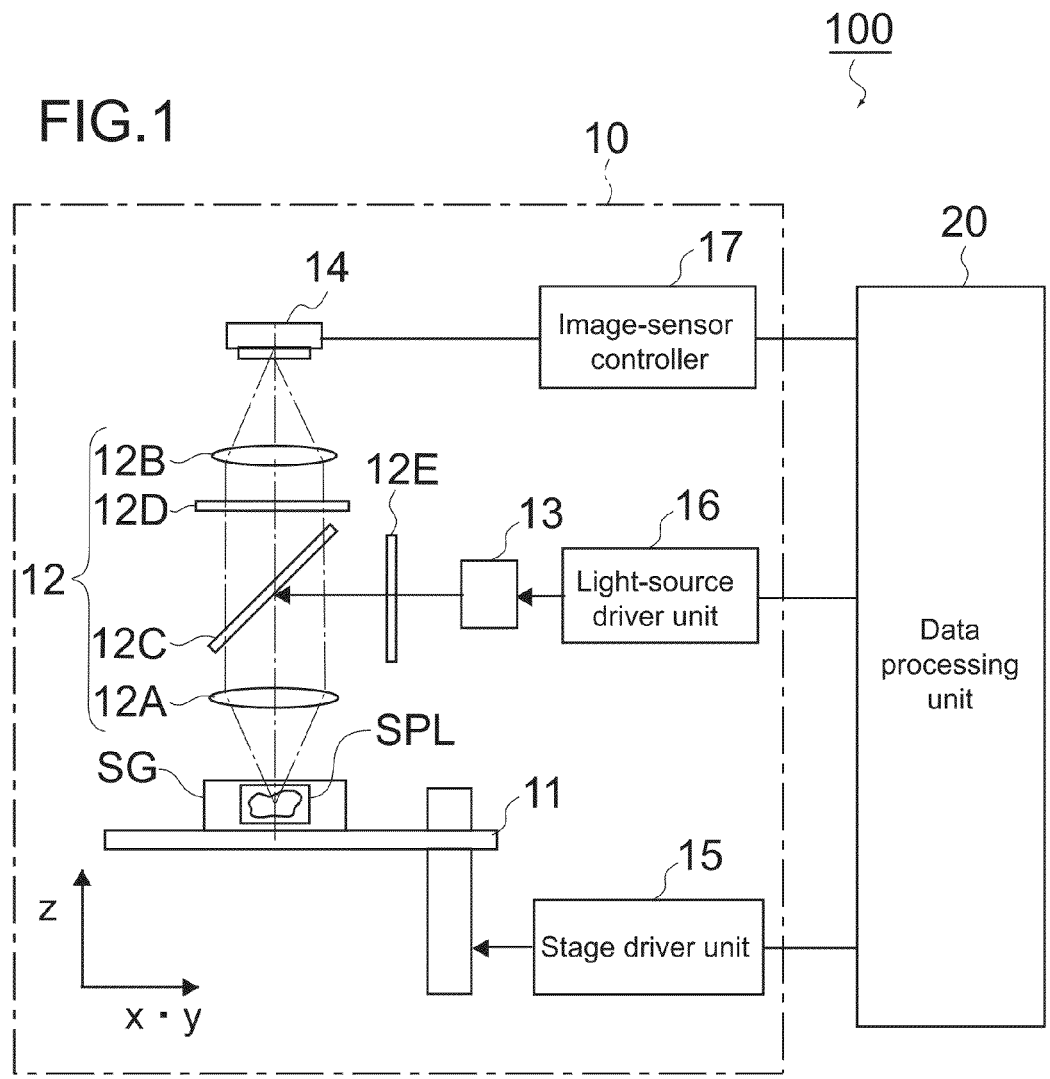
FIG. 1 is a schematic diagram showing an image obtaining apparatus according to a first embodiment of the present technology.

FIG. 1 is a schematic diagram showing an image obtaining apparatus 100 according to a first embodiment. As shown in FIG. 1, the image obtaining apparatus 100 of this embodiment includes a microscope 10 and a data processing unit 20.

[Structure of Microscope]

The microscope 10 includes a stage 11, an optical system 12, a light source 13, and an image sensor 14.

The stage 11 has a mount surface. A biological sample SPL is mounted on the mount surface. Examples of the biological sample SPL include a slice of tissue, a cell, a biopolymer such as a chromosome, and the like. The stage 11 is capable of moving in the horizontal direction (X-Y plane direction) and in the vertical direction (Z-axis direction) with respect to the mount surface.

Figure 2:
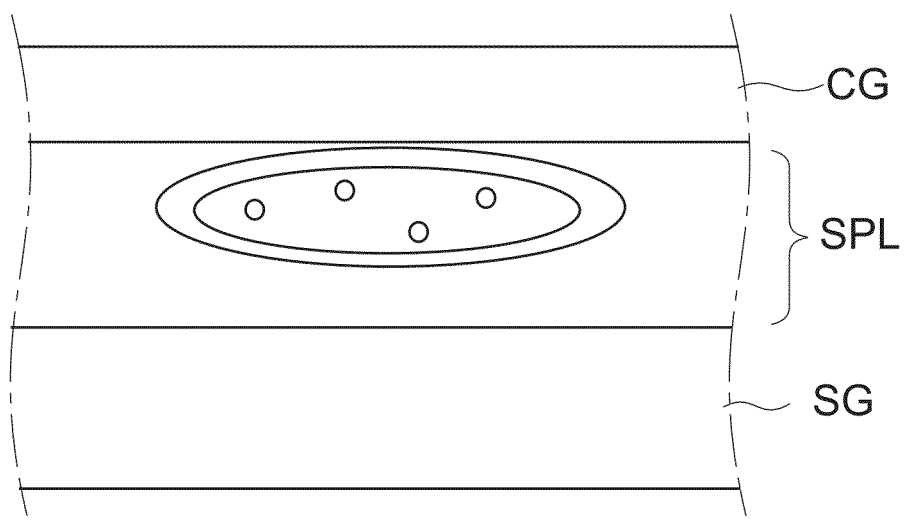
FIG. 2 is a diagram showing a biological sample as a target, whose image is to be obtained by the image obtaining apparatus of FIG. 1.

FIG. 2 is a diagram showing the biological sample SPL mounted on the above-mentioned stage 11. FIG. 2 shows the biological sample SPL in the direction from the side of the stage 11. As shown in FIG. 2, the biological sample SPL has a thickness of several μm to several tens of μm in the Z direction, for example. The biological sample SPL is sandwiched between a slide glass SG and a cover glass CG, and is fixed by a predetermined fixing method. The biological sample SPL is dyed with a fluorescence staining reagent. Fluorescence staining reagent is a stain irradiated with an excitation light from the same light source to thereby emit fluorescence. As the fluorescence staining reagent, for example, DAPI(4',6-diamidino-2-phenylindole), SpAqua, SpGreen, or the like may be used.

With reference to FIG. 1 again, the optical system 12 is arranged above the stage 11. The optical system 12 includes an objective lens 12A, an imaging lens 12B, a dichroic mirror 12C, an emission filter 12D, and an excitation filter 12E. The light source 13 is, for example, a light bulb such as a mercury lamp, an LED (Light Emitting Diode), or the like. Fluorescent labels in a biological sample are irradiated with an excitation light from the light source 13.

In a case of obtaining a fluorescent image of the biological sample SPL, the excitation filter 12E only causes light, which has an excitation wavelength for exciting fluorescent dye, to pass through, out of light emitted from the light source 13, to thereby generate an excitation light. The excitation light, which has passed through the excitation filter and enters the dichroic mirror 12C, is reflected by the dichroic mirror 12C, and is guided to the objective lens 12A. The objective lens 12A condenses the excitation light on the biological sample SPL. Then, the objective lens 12A and the imaging lens 12B magnify the image of the biological sample SPL at a predetermined power, and form the magnified image in an imaging area of the image sensor 14.

When the biological sample SPL is irradiated with the excitation light, the stain emits fluorescence. The stain is bound to each tissue of the biological sample SPL. The fluorescence passes through the dichroic mirror 12C via the objective lens 12A, and reaches the imaging lens 12B via the emission filter 12D. The emission filter 12D absorbs light, which is magnified by the above-mentioned objective lens 12A and has passed through the excitation filter 12E. Part of color light passes through the emission filter 12D. As described above, the imaging lens 12B magnifies an image of the color light, from which outside light is lost. The imaging lens 12B forms an image on the image sensor 14.

As the image sensor 14, for example, a CCD (Charge Coupled Device), a CMOS (Complementary Metal Oxide Semiconductor) image sensor, or the like is used. The image sensor 14 has a photoelectric conversion element, which receives RGB (Red, Green, Blue) colors separately and converts the colors into electric signals. The image sensor 14 is a color imager, which obtains a color image based on incident light.

The data processing unit 20 drives the light source 13. The data processing unit 20 obtains a fluorescent image of the biological sample SPL by using the image sensor 14. The data processing unit 20 stores the fluorescent image as sample data.

[Configuration of Data Processing Unit]

Figure 3:
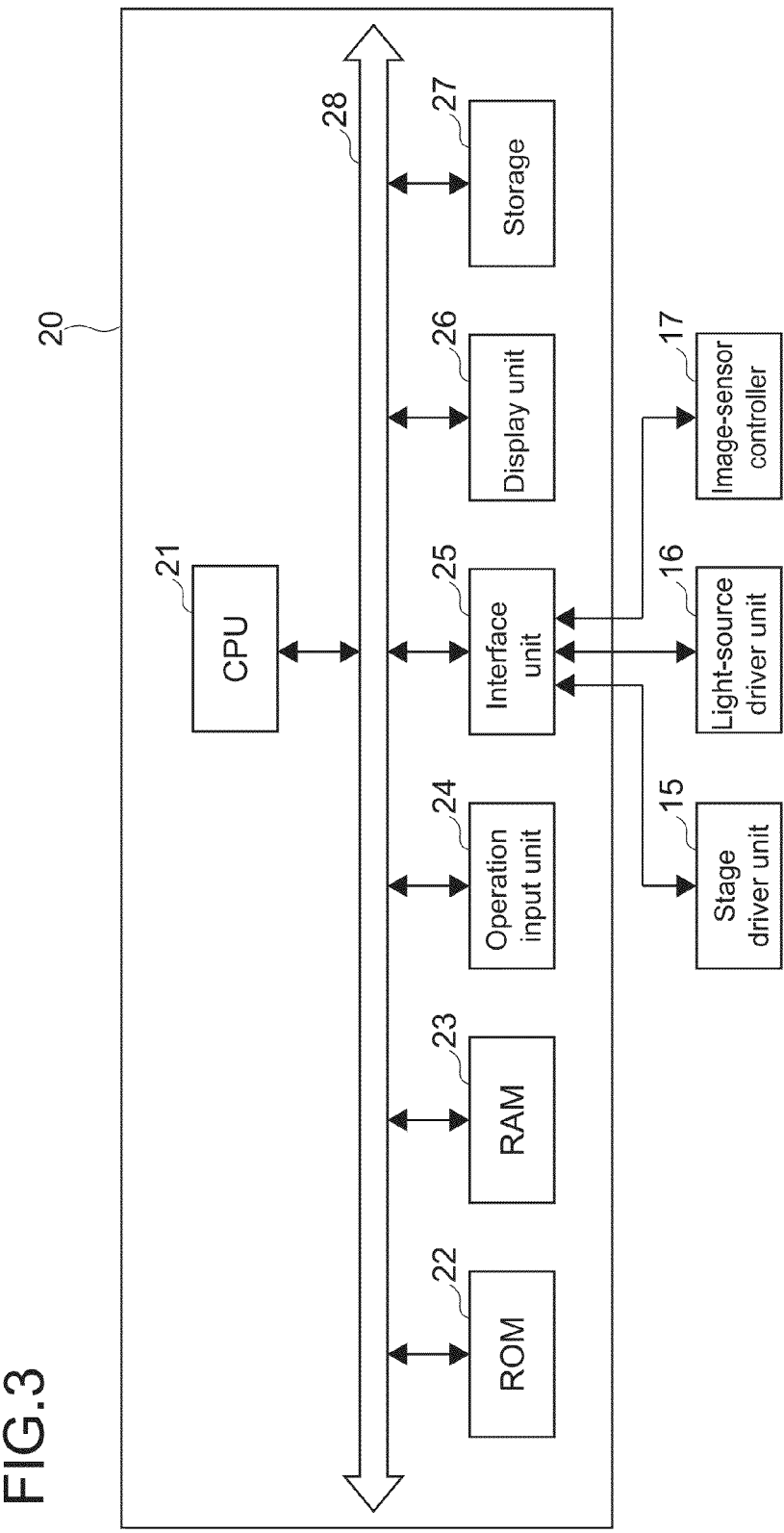
FIG. 3 is a block diagram showing a hardware configuration of a data processing unit of the image obtaining apparatus of FIG. 1.

FIG. 3 is a block diagram showing the hardware configuration of the data processing unit 20.

The data processing unit 20 is configured by, for example, a PC (Personal Computer). The data processing unit 20 stores a fluorescent image of the biological sample SPL, which is obtained from the image sensor 14, as digital image data of an arbitrary-format such as JPEG (Joint Photographic Experts Group), for example.

As shown in FIG. 3, the data processing unit 20 includes a CPU (Central Processing Unit) 21, a ROM (Read Only Memory) 22, a RAM (Random Access Memory) 23, an operation input unit 24, an interface unit 25, a display unit 26, and storage 27. Those blocks are connected to each other via a bus 28.

The ROM 22 is fixed storage for storing data and a plurality of programs such as firmware executing various processing. The RAM 23 is used as a work area of the CPU 21, and temporarily stores an OS (Operating System), various applications being executed, and various data being processed.

The storage 27 is a nonvolatile memory such as an HDD (Hard Disk Drive), a flash memory, or another solid memory, for example. The OS, various applications, and various data are stored in the storage 27. Specifically, in this embodiment, fluorescent image data captured by the image sensor 14 and an image processing application for processing fluorescent image data are stored in the storage 27.

The interface unit 25 is connected to a control board including a stage driver unit 15, a light-source driver unit 16, and an image-sensor controller 17. The stage driver unit 15 drives the stage 11 of the microscope 10. The light-source driver unit 16 drives the light source 13 of the microscope 10. The image-sensor controller 17 drives the image sensor 14 of the microscope 10. The interface unit 25 sends and receives signals to and from the control board and the data processing unit 20 according to a predetermined communication standard.

The CPU 21 expands, in the RAM 23, programs corresponding to instructions received from the operation input unit 24 out of a plurality of programs stored in the ROM 22 or in the storage 27. The CPU 21 arbitrarily controls the display unit 26 and the storage 27 according to the expanded programs.

The operation input unit 24 is an operating device such as a pointing device (for example, mouse), a keyboard, or a touch panel.

The display unit 26 is a liquid crystal display, an EL (Electro-Luminescence) display, a plasma display, a CRT (Cathode Ray Tube) display, or the like, for example. The display unit 26 may be built in the data processing unit 20, or may be externally connected to the data processing unit 20.

[Typical Process of Obtaining Biological Sample Image]

Before describing a process of obtaining a biological sample image by the image obtaining apparatus 100 of this embodiment, a typical process of obtaining a biological sample image and a problem thereof will be described.

Figure 4:
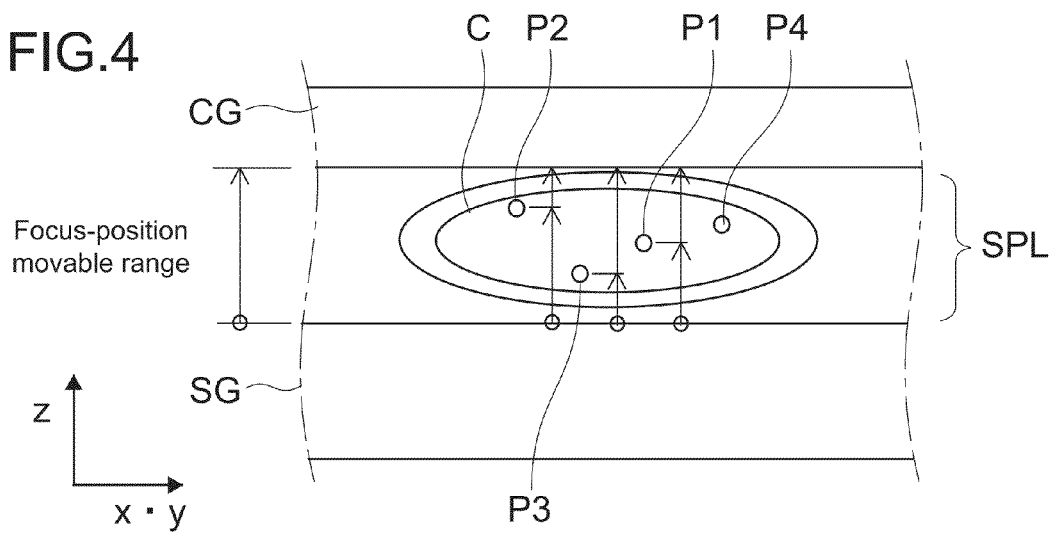
FIG. 4 is a diagram for explaining a process of obtaining a biological sample image by a typical image obtaining apparatus.

FIG. 4 is a diagram for describing a process of obtaining a biological sample image by a typical image obtaining apparatus.

The typical image obtaining apparatus moves a focus position of an optical system in the thickness range of the biological sample SPL in the thickness direction of the biological sample SPL (in FIG. 4, in the vertical direction). Simultaneously, the typical image obtaining apparatus exposes an image sensor to light from the initial time point of movement of the focus position to the final time point of the movement. The typical image obtaining apparatus captures pixel data from the image sensor at the final time point. Finally, one fluorescent image is obtained. In one fluorescent image, images at the respective focus positions over the entire biological sample SPL in the thickness direction of the biological sample SPL are merged.

In this manner, the focus position is moved over the entire biological sample in the thickness direction, and the image sensor is exposed to light simultaneously, whereby a fluorescent image is obtained. However, actually, in the fluorescent image, images of bright points for marking a target (hereinafter, referred to as "fluorescent markers".), which are in the both end portions of the biological sample in the thickness direction, are larger in size than images of fluorescent markers in the center portion. Further, the brightness of the fluorescent markers in the both end portions is lower than the brightness of the fluorescent markers in the center portion. Because of this, in a case of detecting a fluorescent marker based on size and brightness, and in other cases, detection accuracy is lowered.

Figure 5:
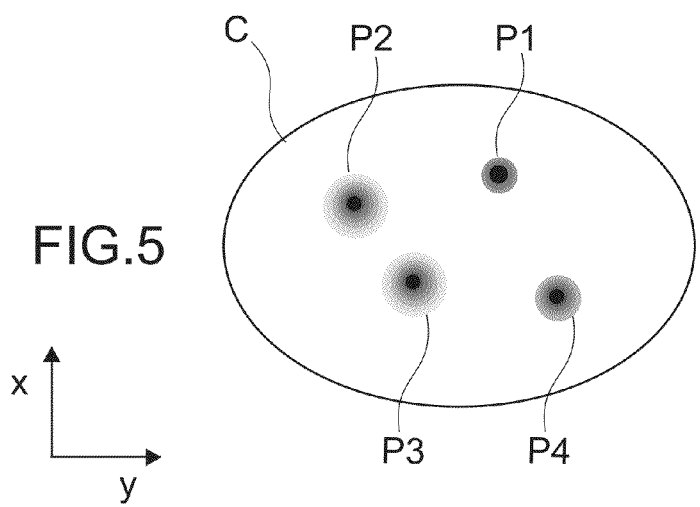
FIG. 5 is a diagram showing an example of a biological sample image obtained by a typical image obtaining apparatus.

In FIG. 4, a fluorescent marker P1, which is in the center portion of the biological sample SPL in the thickness direction, will be described. The focus position gradually comes close to the fluorescent marker P1, the fluorescent marker P1 is brought into focus once, and then the focus position gradually goes away from the fluorescent marker P1. That is, the image of the fluorescent marker P1 gradually changes from a large blurred state to a small clear state, and after that, changes to a large blurred state. Next, a fluorescent marker P2, which in the upper portion of the biological sample SPL, will be described. The focus position comes close to the fluorescent marker P2 from a position more distant than the case of the fluorescent marker P1. Because of this, as shown in FIG. 5, the image of the fluorescent marker P2 in the upper portion of the biological sample SPL is more blurred and is larger than the image of the fluorescent marker P1 in the center portion. A fluorescent marker P3 in the lower portion of the biological sample will be described. Similarly, the fluorescent marker P3 is brought into focus once, and then the focus position goes more distant than the case of the fluorescent marker P1. Because of this, the image of the fluorescent marker P3 is also more blurred and is larger than the image of the fluorescent marker P2 in the center portion. Because of this, in a case of detecting a fluorescent marker based on size and brightness of the fluorescent marker, and in other cases, detection accuracy may be reduced.

Figure 6:
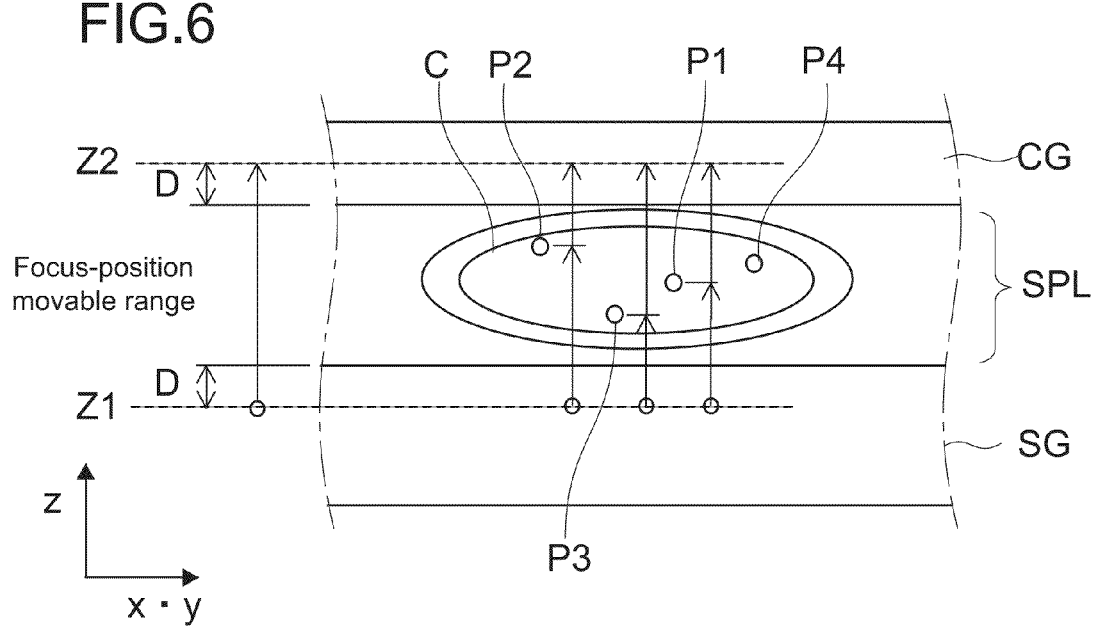
FIG. 6 is a diagram for explaining a process of obtaining a biological sample image by the image obtaining apparatus of FIG. 1.
Figure 7:
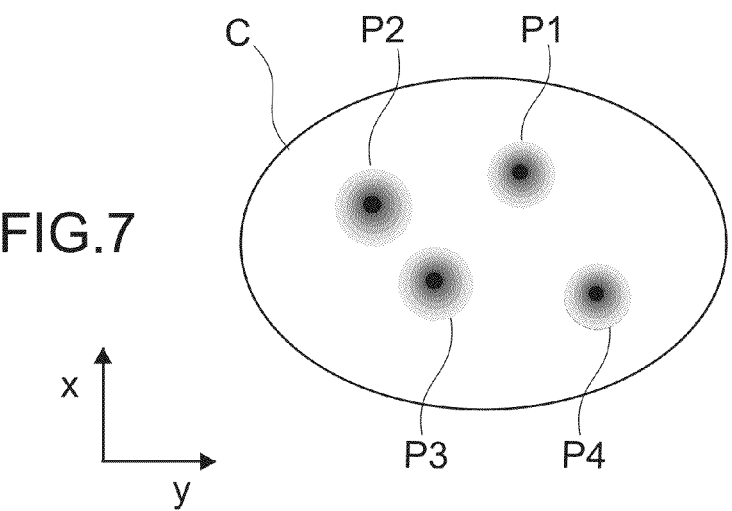
FIG. 7 is a diagram showing an example of a biological sample image obtained by the image obtaining apparatus of FIG. 1.

To solve the above-mentioned problem, as shown in FIG. 6, the image obtaining apparatus 100 of this embodiment moves the focus position of the optical system 12 in an extended range, in which predetermined margins D are added to the both sides of the thickness range of the biological sample SPL. As a result, as shown in FIG. 7, there may be obtained a biological sample image in which images of all fluorescent labels R1 to R4 are blurred approximately uniformly. Because there is obtained a biological sample image in which images of all the fluorescent labels R1 to R4 are blurred approximately uniformly, accuracy of detecting fluorescent markers may be improved, accuracy of measuring brightness and sizes of fluorescent markers may be improved, and the like, for example.

[Specific Process of Obtaining Biological Sample Image]

The CPU 21 of the data processing unit 20 expands, in the RAM 23, a program corresponding to an instruction received from the operation input unit 24 out of a plurality of programs stored in the ROM 22 or the storage 27. The CPU 21 executes the process of obtaining a biological sample image based on the expanded program (image obtaining program).

Figure 8:
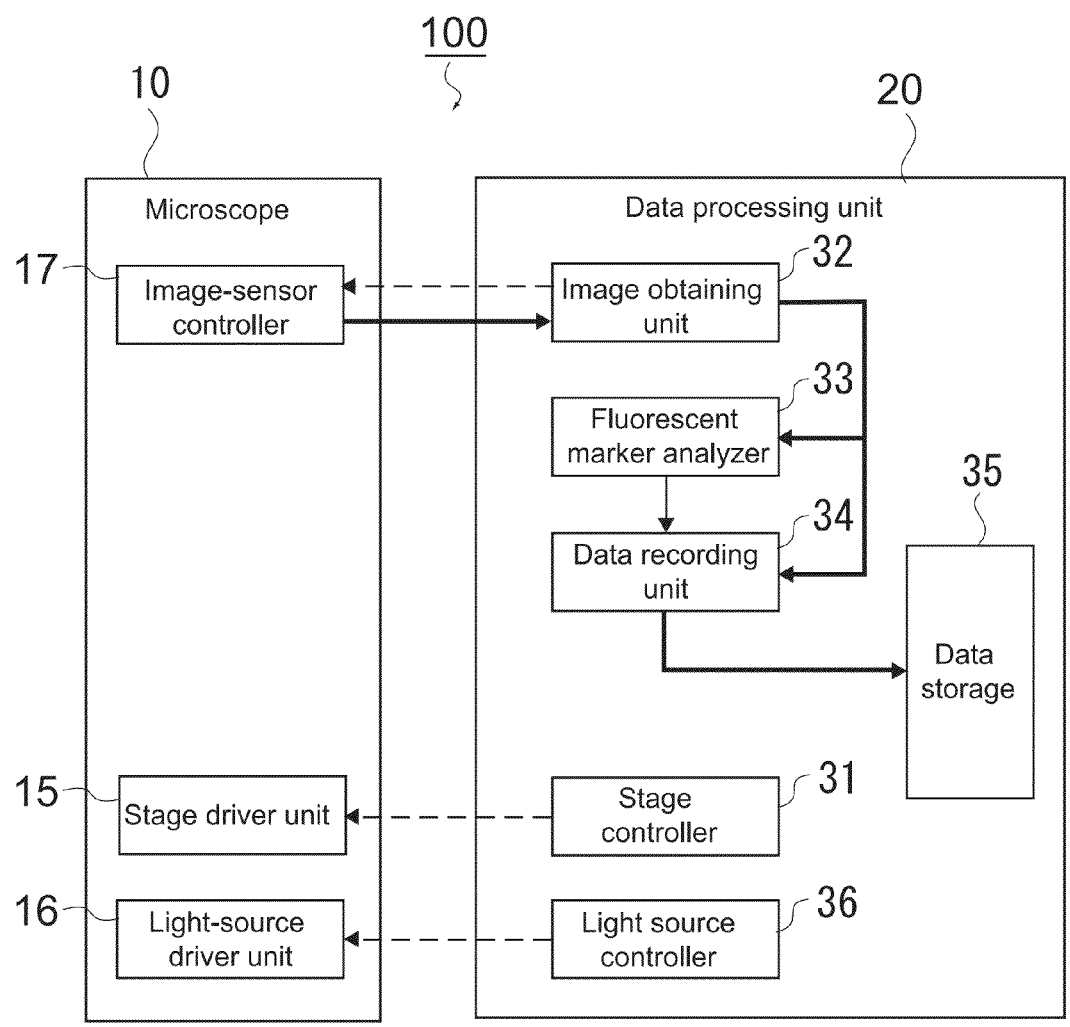
FIG. 8 is a functional block diagram showing a process of obtaining a biological sample image by the image obtaining apparatus of FIG. 1.

FIG. 8 is a functional block diagram for the process of obtaining a biological sample image.

Figure 9:
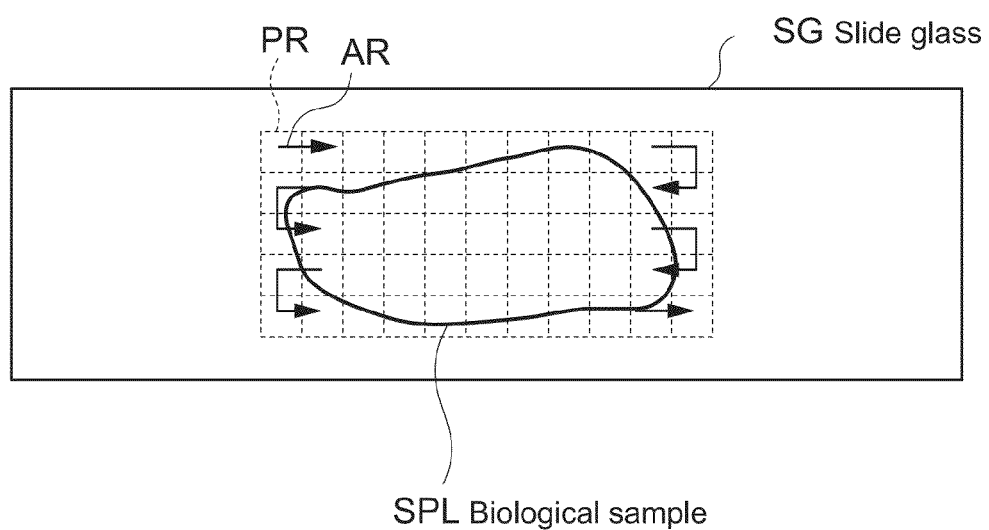
FIG. 9 is a diagram showing imaging target areas imaged by the image obtaining apparatus of FIG. 1.

In FIG. 8, a stage controller 31 (movement controller) sequentially moves the stage 11 such that a target site of the biological sample SPL (hereinafter, this is also referred to as "sample site") is in an imaged area. For example, as shown in FIG. 9, the stage controller 31 (movement controller) allocates the biological sample SPL to the imaged areas AR. Note that, in FIG. 9, areas of the biological sample SPL to be allocated to the imaged areas AR are not overlapped with each other. Alternatively, part of an area may be overlapped with part of an adjacent area.

Further, the stage controller 31 moves the stage 11 in the Z-axis direction (optical-axis direction of the objective lens 12A) every time a target sample site is moved to the imaged area AR. The stage controller 31 controls to move the focus on the sample site in the thickness direction. Here, as shown in FIG. 6, the stage controller 31 moves the stage 11 in the Z-axis direction such that the focus position moves between a first position Z1 and a second position Z2 (extended range). The first position Z1 is distant from the lower end of the thickness range of the biological sample SPL in the lower direction by the predetermined margin D. The second position Z2 is distant from the upper end of the thickness range of the biological sample SPL in the upper direction by the predetermined margin D.

An image obtaining unit 32 (light-exposure controller) sends an instruction to the image-sensor controller 17 every time the stage controller 31 moves the target sample site to the imaged area AR. The instruction is to expose the image sensor 14 to light from the initial time point of movement of the stage 11 in the Z-axis direction to the final time point. At the final time point of the movement of the stage 11 in the Z-axis direction, the image obtaining unit 32 obtains images from the image sensor 14 via the image-sensor controller 17. The images are images of the sample sites obtained by light-exposure between the final time point of the movement and the initial time point of the movement. Then, the image obtaining unit 32 combines the images of the sample sites allocated to the imaged areas AR by using a predetermined combining algorithm, respectively, to thereby generate an entire biological sample image.

A fluorescent marker analyzer 33 (analyzer) detects fluorescent markers, which mark target living-body tissues (hereinafter, referred to as "target markers".), from the biological sample image generated by the image obtaining unit 32. Setting information is set to the fluorescent marker analyzer 33. For example, the setting information includes a color (hereinafter, referred to as "target marker color".) of the target markers, and a color (hereinafter, referred to as "nucleus marker color".) of fluorescent markers. The fluorescent markers mark cell nuclei (hereinafter, referred to as "nucleus markers"). Further, in a case where fluorescent markers for marking control genes (hereinafter, referred to as "control markers".) are used, the number of the control genes in a normal cell nucleus is set. Further, in this case, the color (hereinafter, referred to as "control marker color".) of the fluorescent markers for marking a control gene (hereinafter, referred to as "control markers".) is also set.

The setting information is uniquely determined according to use conditions such as a manufacturer of a probe to be used for the fluorescence stain, and the kind of the fluorescent marker. Specifically, for example, in the case of HER-2 DNA probe kit (Abbott Japan Co., Ltd.), "red" is set as the target marker color of HER-2 gene, and "blue" is set as the nucleus marker color. Further, in this case, the control gene is a gene next to HER-2 gene in a chromosome. "Green" is set as the control marker color of the control gene. In general, "2" is set as the number.

Next, a method of detecting fluorescent markers by the fluorescent marker analyzer 33 will be described.

The fluorescent marker analyzer 33 detects cell nuclei from a biological sample image generated by the image obtaining unit 32. The cell nuclei are areas next to pixels, each of which corresponds to the nucleus marker color set as a color of cell nuclei, and has the brightness equal to or more than a threshold.

Subsequently, the fluorescent marker analyzer 33 detects target markers and control markers in the detected cell nuclei. Here, the biological sample image is obtained by exposing the image sensor 14 to light while moving the focus position in the range extended in the thickness direction of the biological sample SPL. Because of this, the target markers and the control markers are marked as approximately-circular blurred bright points in a biological sample image. Further, as shown in FIG. 6, the biological sample image is obtained by exposing the image sensor 14 to light while moving the focus position from the first position Z1 to the second position Z2. The first position Z1 is distant from the lower end of the thickness range of the biological sample SPL in the lower direction by the predetermined margin D. The second position Z2 is distant from the upper end of the thickness range of the biological sample SPL in the upper direction by the predetermined margin D. As a result, all the target markers and all the control markers are blurred approximately uniformly in the biological sample image.

The fluorescent marker analyzer 33 detects, as target markers, areas (bright points) satisfying the following condition. That is, the predetermined number (areas) or more of pixels, which exhibit the marker color set for the target markers and have the brightness equal to or more than a threshold, are next to each other to thereby form an approximately-circular shape. Similarly, the fluorescent marker analyzer 33 detects, as control markers, areas (bright points) satisfying the following condition. That is, the predetermined number (areas) or more of pixels, which exhibit the marker color set for the control markers and have the brightness equal to or more than a threshold, are next to each other to thereby form an approximately-circular shape. Here, the condition for determining the target markers may be the same to or different from the condition for determining the control markers except for the exhibited marker color.

As described above, areas (bright points), which satisfy the condition in which the predetermined number (areas) or more of pixels having the brightness equal to or more than a threshold are next to each other, are detected as the target markers or the control markers. As a result, the fluorescent marker analyzer 33 completely detects all the target markers and control markers, which are marked as approximately uniformly blurred bright points in the biological sample image.

Further, the fluorescent marker analyzer 33 measures the brightness average and the pixel number showing the area of the detected target markers. The fluorescent marker analyzer 33 measures the brightness average and the pixel number of the detected control markers.

Meanwhile, a data recording unit 34 combines biological sample images of each sample site, which are generated by the image obtaining unit 32, to thereby generate one biological sample image. The data recording unit 34 encodes the one biological sample image to thereby obtain sample data of the predetermined compression format such as JPEG (Joint Photographic Experts Group), and records the sample data in data storage 35. This process may be performed before the fluorescent marker analyzer 33 detects the fluorescent markers.

The data recording unit 34 receives measurement results of the fluorescent markers from the fluorescent marker analyzer 33. Then, the data recording unit 34 records the measurement results data in the data storage 35 in association with sample data.

Figure 11:
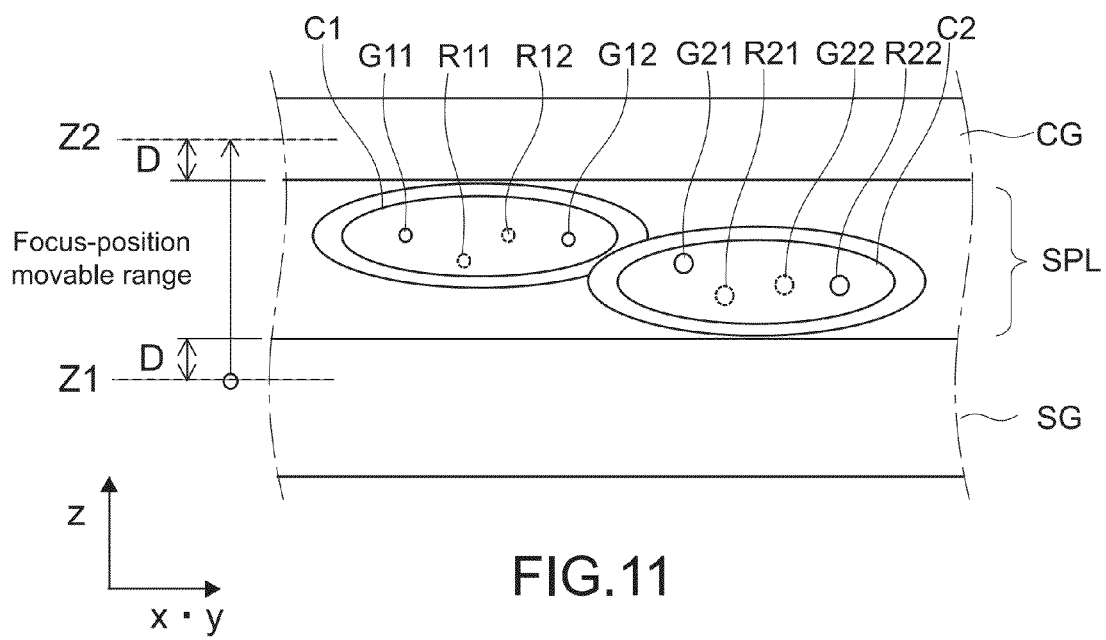
FIG. 11 is a diagram showing an example of a biological sample corresponding to the recording example of the detected results of fluorescent markers shown in FIG. 10.
Figure 12:
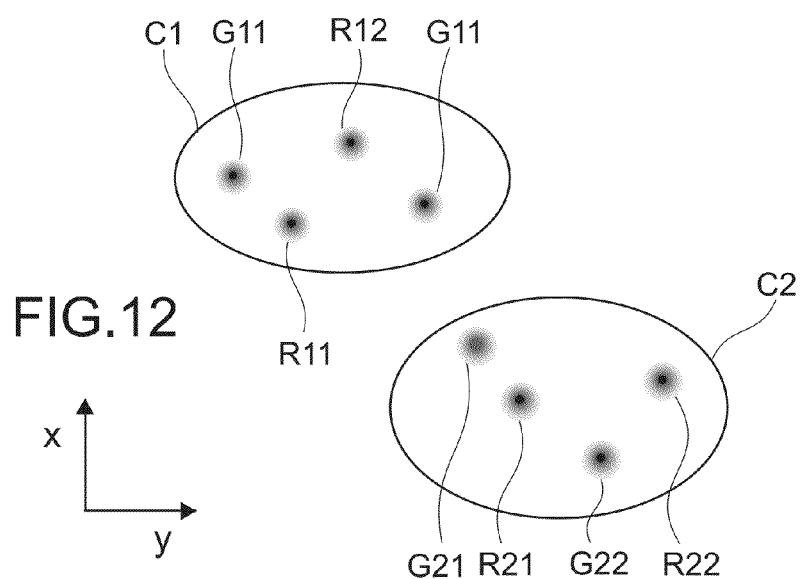
FIG. 12 is a diagram showing a biological sample image obtained by the biological sample of FIG. 11.

FIG. 10 shows recording examples of measurement results of fluorescent markers from a biological sample image (FIG. 12) measured by the fluorescent marker analyzer 33. FIG. 12 is a biological sample image obtained from a biological sample shown in FIG. 11 by the image obtaining apparatus 100 of this embodiment.

In this example, two cell nuclei C1, C2 are detected. In one cell nucleus C1, two target markers R11, R12 and two control markers G11, G12 are detected. In the other cell nucleus C2, two target markers R21, R22 and two control markers G21, G22 are detected. A serial number, which identifies each target marker in each cell nucleus, is given to each target marker detected in each cell nucleus C1, C2. A serial number, which identifies the control marker in each cell nucleus, is given to each control marker detected in each cell nucleus C1, C2. Note that the kind of the marker is identified by color. Further, the brightness average and the pixel number showing the marker areas are recorded in the data storage 35 in relation with each target marker and each control marker.

Note that, in addition to the information shown in FIG. 10, for example, information on the name of a patient, the sex of the patient, the age of the patient, the date of obtaining the biological sample SPL, and the like are given to the recorded data of the measurement results of the fluorescent markers measured by the fluorescent marker analyzer 33.

As described above, according to the configuration of this embodiment, the image obtaining unit 32 obtains the biological sample image by exposing the image sensor 14 to light while moving the focus position from the first position Z1 to the second position Z2. The first position Z1 is distant from the lower end of the thickness range of the biological sample SPL in the lower direction by the predetermined margin D. The second position Z2 is distant from the upper end of the thickness range of the biological sample SPL in the upper direction by the predetermined margin D.

All the target markers and all the control markers are blurred approximately uniformly in the biological sample image obtained as described above. Therefore the fluorescent marker analyzer 33 detects areas (bright points), which satisfy the condition in which the predetermined number (areas) or more of pixels having the brightness equal to or more than a threshold are next to each other, as the target markers or the control markers. In this case, the fluorescent marker analyzer 33 completely detects all the target markers and control markers. Further, the fluorescent marker analyzer 33 may accurately measure the brightness average and the pixel number showing the area of the detected target markers. The fluorescent marker analyzer 33 measures the brightness average and the pixel number of the detected control markers.

The values of the margins D will be described. The distance between the lower end of the thickness range of the biological sample SPL and the lower end of the focus position is referred to as D1. The distance between the upper end of the same range and the upper end of the focus position is referred to as D2. D1 is not necessarily equal to D2. However, D1 is preferably equal to D2 because the blur of fluorescent labels in the upper portion of the thickness range of the biological sample SPL is made similar to the blur of fluorescent labels in the lower portion as much as possible.

Further, if the margins D are too small, the difference of brightness and the difference of area sizes between fluorescent markers in the center portion of the thickness range of a biological sample and fluorescent markers in the both ends of the same range may not be reduced enough. Meanwhile, if the margins D are too large, the brightness of all the fluorescent markers is too low. As a result, it is difficult to detect the fluorescent markers. The preferable specific value or range of the margin D depends on various conditions such as the thickness of the biological sample SPL and the numerical aperture NA (focus depth) of the objective lens 12A of the optical system 12. In view of this, for example, it is one method to change the various conditions to find out the most preferable value. According to this method, for example, fluorescent markers are blurred at approximately the same level in the case where the numerical aperture NA is 0.8 and the margin D is 3 μm.

Note that, in the structure of the microscope 10 of the above-mentioned embodiment, the objective lens 12A may be an eyepiece lens.

Further, in the above-mentioned embodiment, the stage 11 is moved to thereby move the focus position. Alternatively, the objective lens 12A of the optical system 12 may be moved.

In the above-mentioned embodiment, the data processing unit 20 includes the data storage 35. Biological sample images and detected results of fluorescent markers are recorded in the data storage 35. Alternatively, they may be recorded in external storage.

The microscope 10 may be connected to the data processing unit 20 not by a bus transmission path, but by a wired or wireless transmission medium such as a local area network, the Internet, or digital satellite broadcasting.

Note that the present technology may employ the following configurations.

(1) An image obtaining apparatus, comprising:

a light source configured to irradiate a biological sample having a fluorescent label with an excitation light, the excitation light exciting the fluorescent label;

an optical system including an objective lens, the objective lens being configured to magnify an imaging target of the biological sample;

an image sensor configured to form an image of the imaging target magnified by the objective lens;

a movement controller configured to move a focus position of the optical system in an extended range, the extended range being obtained by adding predetermined margins to both ends of the imaging target in a thickness range; and a light-exposure controller configured to expose the image sensor to light while moving the focus position of the optical system in the extended range.

(2) The image obtaining apparatus according to (1), wherein the predetermined margins at the both sides of the imaging target in the thickness range are the same.

(3) The image obtaining apparatus according to (1) or (2), further comprising:

a light source configured to irradiate a fluorescent label with an excitation light, wherein the light-exposure controller is configured to expose the image sensor to light while moving the focus position of the optical system in the extended range, to thereby obtain a fluorescent image of the imaging target.

(4) The image obtaining apparatus according to any one of (1) to (3), further comprising:
an analyzer configured
to detect the fluorescent label from the obtained fluorescent image, and
to obtain the brightness and size of the fluorescent label.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An image obtaining apparatus, comprising:
   a light source configured to irradiate a biological sample having a fluorescent label with an excitation light, the excitation light exciting the fluorescent label;
   an optical system including an objective lens, the objective lens being configured to magnify an imaging target of the biological sample;
   an image sensor configured to form an image of the imaging target magnified by the objective lens;
   a movement controller configured to move a focus position of the optical system in an extended range, the extended range being obtained by adding predetermined margins to both ends of the imaging target in a thickness range; and
   a light-exposure controller configured to expose the image sensor to light while moving the focus position of the optical system in the extended range,
   wherein the predetermined margins are set such that blurring amounts in biological sample images obtained by the image sensor for a plurality of fluorescent labels disposed at different positions in a thickness direction of the biological sample are approximately uniform.

2. The image obtaining apparatus according to claim 1, wherein
   the predetermined margins at the both sides of the imaging target in the thickness range are the same.

3. The image obtaining apparatus according to claim 2, further comprising:
   a light source configured to irradiate a fluorescent label with an excitation light, wherein
   the light-exposure controller is configured to expose the image sensor to light while moving the focus position of the optical system in the extended range, to thereby obtain a fluorescent image of the imaging target.

4. The image obtaining apparatus according to claim 3, further comprising:
   an analyzer configured
   to detect the fluorescent label from the obtained fluorescent image, and
   to obtain the brightness and size of the fluorescent label.

5. An image obtaining method, comprising:
   irradiating a biological sample having a fluorescent label with an excitation light, the excitation light exciting the fluorescent label;
   moving a focus position of an optical system in an extended range, the extended range being obtained by adding predetermined margins to both ends of an imaging target of the biological sample in a thickness range, the optical system including an objective lens, the objective lens being configured to magnify the imaging target; and
   exposing the image sensor to light while moving the focus position of the optical system in the extended range,
   wherein the predetermined margins are set such that blurring amounts in biological sample images obtained by the image sensor for a plurality of fluorescent labels disposed at different positions in a thickness direction of the biological sample are approximately uniform.

6. A nontransitory computer readable medium including executable instructions for an image obtaining program, the instructions configured to cause a computer to execute the steps of:
   irradiating a biological sample having a fluorescent label with an excitation light from a light source, the excitation light exciting the fluorescent label;
   moving a focus position of an optical system in an extended range, the extended range being obtained by adding predetermined margins to both ends of an imaging target of the biological sample in a thickness range, the optical system including an objective lens, the objective lens being configured to magnify the imaging target; and
   exposing the image sensor to light while moving the focus position of the optical system in the extended range,
   wherein the predetermined margins are set such that blurring amounts in biological sample images obtained by the image sensor for a plurality of fluorescent labels disposed at different positions in a thickness direction of the biological sample are approximately uniform.

* * * * *